US012788310B2

(12) United States Patent
Swentek et al.

(10) Patent No.: US 12,788,310 B2
(45) Date of Patent: Nov. 10, 2026

(54) NON-INVASIVE CERVICAL DILATION MONITORING

(71) Applicant: THE REGENTS OF THE UNIVERSITY OF CALIFORNIA, Oakland, CA (US)

(72) Inventors: Lourdes Swentek, Orange, CA (US); Thomas Milner, Irvine, CA (US); Nitesh Katta, Irvine, CA (US); Yona Tadir, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 415 days.

(21) Appl. No.: 18/453,189

(22) Filed: Aug. 21, 2023

(65) Prior Publication Data

US 2024/0057935 A1 Feb. 22, 2024

Related U.S. Application Data

(60) Provisional application No. 63/373,128, filed on Aug. 22, 2022.

(51) Int. Cl.
*A61B 5/00* (2006.01)
*A61B 5/1455* (2006.01)

(52) U.S. Cl.
CPC ............ *A61B 5/435* (2013.01); *A61B 5/0095* (2013.01); *A61B 5/14551* (2013.01); *A61B 5/6852* (2013.01)

(58) Field of Classification Search
CPC ..... A61B 5/435; A61B 5/0095; A61B 5/6852; A61B 5/1459; A61B 5/02411; A61B 5/4362
See application file for complete search history.

(56) References Cited

U.S. PATENT DOCUMENTS

| | | | | |
|---|---|---|---|---|
| 5,487,740 A * | 1/1996 | Sulek | A61B 18/28 | 606/17 |
| 10,993,606 B2 * | 5/2021 | Weitzner | A61B 1/018 | |
| 2008/0009732 A1 * | 1/2008 | Sogade | A61B 8/12 | 600/443 |
| 2020/0337683 A1 * | 10/2020 | Meduri | A61B 10/02 | |

OTHER PUBLICATIONS

"Transurethral light delivery for prostate photoacoustic imaging" by M.A. Bell et al. J Biomed Optics. 20(3) 2015 (Year: 2015).*

* cited by examiner

*Primary Examiner* — Jason M Ip
(74) *Attorney, Agent, or Firm* — NGUYEN TARBET IP LAW

(57) ABSTRACT

Internal cervical exams during labor pose multiple challenges, including infection risk, subjectivity, invasiveness, and discomfort. A monitoring system described herein enables non-invasive and accurate measurement of cervical dilation and assessment of the baby's station. By inserting a narrow linear ultrasound probe through the working channel, high-resolution ultrasound images of the cervix can be obtained, eliminating the need for painful and subjective exams, reducing infection risk, and enhancing patient comfort. Moreover, the ultrasound capability allows for potential monitoring of maternal and fetal blood oxygenation levels, providing a comprehensive picture of fetal well-being.

17 Claims, 8 Drawing Sheets

Cervical Effacement

Cervix is 50% effaced and not dilated | Cervix is 100% effaced and dilated to 3 cm | Cervix is fully dilated to 10 cm Cervical Effacement Cervix is 50% effaced and not dilated Cervix is 100% effaced and dilated to 3 cm Cervix is fully dilated to 10 cm 2D Image 3D Image

| | Dilation (mm) |
|---|---|
| Attempt 1 | 25 |
| Attempt 2 | 26.5 |
| Attempt 3 | 25.5 |
| Attempt 4 | 27 |
| Attempt 5 | 25 |
| | n = 5 |
| | Range = 25-27 |
| | Average = 25.8 |

NON-INVASIVE CERVICAL DILATION MONITORING

CROSS-REFERENCES TO RELATED APPLICATIONS

This application is a non-provisional and claims benefit of U.S. Provisional Application No. 63/373,128 filed Aug. 22, 2022, the specification of which is incorporated herein in their entirety by reference.

FIELD OF THE INVENTION

The present invention features systems and methods that allow for an accurate and non-invasive way to determine cervical dilation, as well as intrapartum fetal monitoring.

BACKGROUND OF THE INVENTION

Approximately 4 million babies per year are born in the United States. During these deliveries, women in active labor undergo several manual exams to check for cervical dilation and progression of labor. These vaginal exams assist in determining whether the pregnancy is progressing and allows for an assessment of the position of the baby as well as the amount of cervical effacement and dilation that has occurred. There are, however, several problems with an internal cervical exam. First, suppose the membranes (i.e., the amniotic sac) have ruptured during active labor. In that case, an internal exam can lead to the introduction of bacteria which puts the mother and baby at risk for infection. Likewise, vaginal exams are subjective, and if performed by different people, the amount of cervical dilation will differ. Lastly, the vaginal exam is invasive and uncomfortable and can lead to the premature rupture of membranes (i.e., the amniotic sac).

Currently, internal exams are the gold standard for determining cervical effacement and dilation, despite being incredibly subjective and invasive. Over the years, this has sparked interest in tackling the issue of measuring cervical dilation in a non-invasive and more accurate manner. Mechanical and electromechanical cervimeters have been developed to capture dilation accurately but involve an even more invasive method to provide a readout. Briefly, cervimeters involve fixing coils or a spring-loaded clip or magnets to either side of the cervix. Although the measurement of cervical dilation is more accurate, these devices create an even more invasive and painful method that continues to pose an infectious risk. Currently, the only way to determine cervical dilation is with the examiner's finger.

Conversely, the present invention provides a method that not only allows for a more accurate method to measure cervical effacement and dilation but also aims to provide a non-invasive method for physiologic changes. The innovative methods and systems herein have the potential to revolutionize cervical examination practices, improving patient experience and enhancing obstetric care.

BRIEF SUMMARY OF THE INVENTION

It is an objective of the present invention to provide methods, systems, and devices that allow for an accurate and non-invasive way to determine cervical effacement and dilation, as specified in the independent claims. Embodiments of the invention are given in the dependent claims. Embodiments of the present invention can be freely combined with each other if they are not mutually exclusive.

The present invention features an ultrasound transceiver placement and imaging approach that allows rapid and precise measurement of cervical effacement and cervical dilation using relatively standard imaging systems. The ultrasound transceiver can function conventionally by emitting and receiving ultrasound energy or as an optoacoustic receiver. When operating as an optoacoustic receiver, short-pulsed light of selected wavelengths is directed toward the cervix and absorbed by target chromophores (e.g., oxy- or deoxy-hemoglobin, lipids, or melanin) and generates a sound wave that the ultrasound transceiver can detect. Choice of ultrasound frequency (7-25 Mhz or higher) provides clear resolution (as low as 0.1 mm or lower) at depths up to 9 cm or longer and an image sector width of 90 degrees. In some embodiments, the present invention allows for 3D ultrasound imaging with ultrasound transceiver technology to incorporate multiple arrays or matrix arrays of transceivers while still maintaining relatively small sizes.

In some embodiments, the present invention may also feature a system for monitoring the progression of labor and obtaining physiological measurements of a fetus during childbirth. The system may comprise a urinary catheter, a working channel attached (e.g., permanently attached or temporarily attached) to the catheter, and an ultrasound transceiver device disposed in the lumen of the working channel. In some embodiments, the working channel comprises a lumen, a proximal end, and a distal end. In other embodiments, the working channel comprises a lumen, a proximal end, a distal end, and a cap attached to a distal end of the working channel. In some embodiments, the cap is detachable. In some embodiments, the system further comprises a light-emitting optical fiber inserted into the lumen of the working channel. In some embodiments, the end of the ultrasound transceiver device is at or near a distal end of the working channel. The ultrasound transceiver device may be configured to be inserted or removed from the working channel.

In some embodiments, the present invention may also feature a system for monitoring the progression of labor and obtaining physiological measurements of a fetus during childbirth. The system may comprise a urinary catheter, a working channel removable or attached to the urinary catheter, and an ultrasound transceiver device disposed in the lumen of the working channel. In some embodiments, the working channel comprises a lumen, a proximal end, and a distal end. In other embodiments, the working channel comprises a lumen, a proximal end, a distal end, and a cap attached to a distal end of the working channel. In some embodiments, the cap is detachable. In some embodiments, the system further comprises a light-emitting optical fiber inserted into the lumen of the working channel. In some embodiments, the end of the ultrasound transceiver device is at or near a distal end of the working channel. The ultrasound transceiver device may be configured to be inserted or removed from the working channel.

In other embodiments, the system may comprise a catheter having a lumen and an ultrasound transceiver device inserted into the lumen of the catheter. In some embodiments, the system further comprises a light-emitting optical fiber inserted into the lumen of the catheter. In some embodiments, the end of the ultrasound transceiver device is at or near a distal end of the catheter. The ultrasound transceiver device may be configured to be inserted or removed from the catheter.

The aforementioned monitoring systems may further comprise an ultrasound transceiver control module operably connected to the ultrasound transceiver device.

In some embodiments, the present invention features a method of monitoring progression of labor and obtaining physiological measurements of a fetus during childbirth. The method may comprise inserting a monitoring system as described herein into a urethra and urinary bladder of a pregnant female during labor and obtaining physiological measurements of a cervical region and a uterus region of the pregnant female during labor. The ultrasound transceiver device transmits and receives ultrasound signals. In some embodiments, the ultrasound transceiver device receives optoacoustic signals. In some embodiments, the ultrasound transceiver device transmits ultrasound signals from 7 MHz to 25 MHz. In some embodiments, the ultrasound transceiver device transmits ultrasound signals at a depth of 9 cm. The ultrasound transceiver device can create a 3D ultrasound image.

In some embodiments, the present invention features a method of monitoring the progression of labor and obtaining physiological measurements of a fetus during childbirth. The method may comprise inserting a catheter into a urethra and urinary bladder of a pregnant female during labor, inserting an ultrasound transceiver device into said catheter, and obtaining physiological measurements of a cervical region and a uterus region of the pregnant female during labor. The ultrasound transceiver device transmits and receives ultrasound signals. In some embodiments, the ultrasound transceiver device receives optoacoustic signals.

The aforementioned methods may further comprise introducing a light source, wherein the light source is inserted into the lumen of the working channel. In one embodiment, the light source is a light-emitting optical fiber. In some embodiments, the ultrasound transceiver device is configured to receive photoacoustic signals generated by the light source. The light source (e.g., the light-emitting optical fiber) may propagate a photoacoustic light source, e.g., a photoacoustic excitation light. In some embodiments, the photoacoustic excitation light is absorbed by tissue chromophores, including but not limited to oxyhemoglobin, deoxyhemoglobin, or a combination thereof. The tissue chromophores may generate a sonic wave that is measured by the ultrasound transceiver device.

The systems and methods described herein allow for accurate measurements of cervical dilation, intrapartum fetal monitoring, monitoring blood oxygenation of the fetus and/or the pregnant female, or a combination thereof.

The present invention takes advantage of the use of urinary catheters during labor. Epidurals have become more commonplace to assist pain management and allow mothers to be awake and alert for labor. However, epidurals can slow the progression of pregnancy. Moreover, when they receive an epidural, women also receive a catheter in order to empty the bladder. Likewise, high-risk pregnancies will occasionally employ a urinary catheter. Therefore, the present invention utilizes the catheter as a conduit to the cervix to avoid painful, invasive, and subjective cervical exams.

One of the unique and inventive technical features of the present invention is the combination of a urinary catheter and a removable (e.g., a temporarily attached) working channel comprising a cap, or alternatively, a urinary catheter with a permanently attached working channel comprising a cap. Without wishing to limit the invention to any theory or mechanism, it is believed that the technical feature of the present invention advantageously provides for a completely sterile environment for the introduction of the ultrasound device. None of the presently known prior references or work has the unique, inventive technical feature of the present invention.

Briefly, the present invention uses a narrow linear ultrasound probe inserted into the working channel as described herein. Through the bladder, the ultrasound probe can image the cervix and provide an accurate depiction of the dynamic changes of the cervix and the baby's station in real time. Additionally, a light-emitting optical fiber may be incorporated into the working channel, which can emit short pulses of light at selected wavelengths that are then absorbed by selected chromophores in the tissue of the pregnant female or fetus. Without wishing to limit the invention to any theory or mechanism, it is believed that the technical feature of the present invention advantageously provides for a noninvasive method of accurately measuring cervical dilation. The methods and systems described herein would eliminate the pain and invasive nature of a manual exam and provide an objective and quantifiable measurement of cervical dilation. Additionally, there would be no chance of rupturing membranes or causing an infection that can directly reach the fetus or the uterus.

Furthermore, using an ultrasound transceiver device combined with a light-emitting optical fiber and optoacoustic signal recording may be able to continuously monitor the blood oxygenation levels of the mother and fetus. Currently, the only way to determine how a fetus is doing during labor is by monitoring the heart rate, which may not give an entire diagnostic picture of the mother, the fetus, or the progression of labor. Another invasive procedure performed to determine if the baby is getting enough oxygen and determine the blood pH is done by collecting a small amount of blood in a thin tube. None of the presently known prior references or work has the unique, inventive technical features of the present invention.

Furthermore, the prior references teach away from the present invention. For example, prior methods to determine cervical dilation are invasive, subjective, and/or unquantifiable.

Furthermore, the inventive technical features of the present invention contributed to a surprising result. For example, the combination of ultrasound and optoacoustic in a single catheter is an unexpected combination to monitor the physiological state of both the mother and fetus as well as document the delivery process and progression. Another example is introducing a diffuse optical probing method that relies on monte carlo estimation to determine quantities like local tissue oxygenation, hemoglobin/oxyhemoglobin (hb/hbo2) relative concentration, and speckle phelemography. The high-frequency ultrasound image allows for estimating layer thicknesses which can then be used to determine the monte carlo simulations for estimating optical signals from a diffuse optical probe.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

The features and advantages of the present invention will become apparent from a consideration of the following detailed description presented in connection with the accompanying drawings in which.

Figure 1:
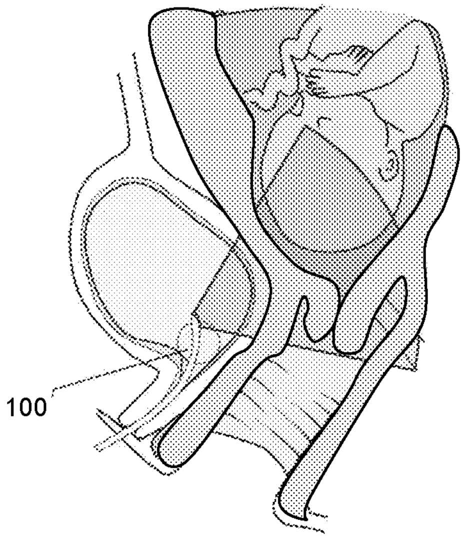
FIG. 1 shows an overview of a schematic of a device as described herein comprising an ultrasound transceiver during operation with ultrasound detection.
Figure 1:
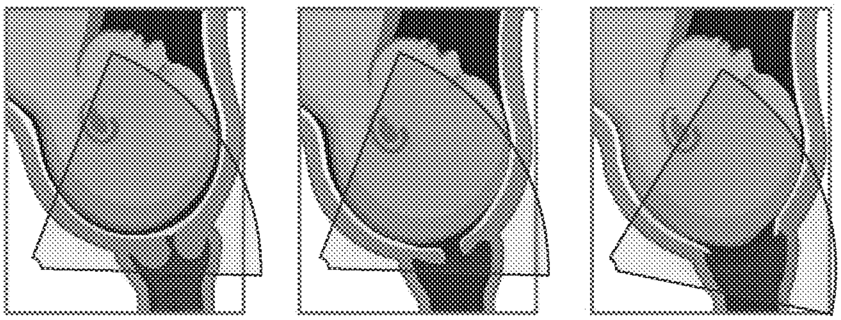
Figure 2:
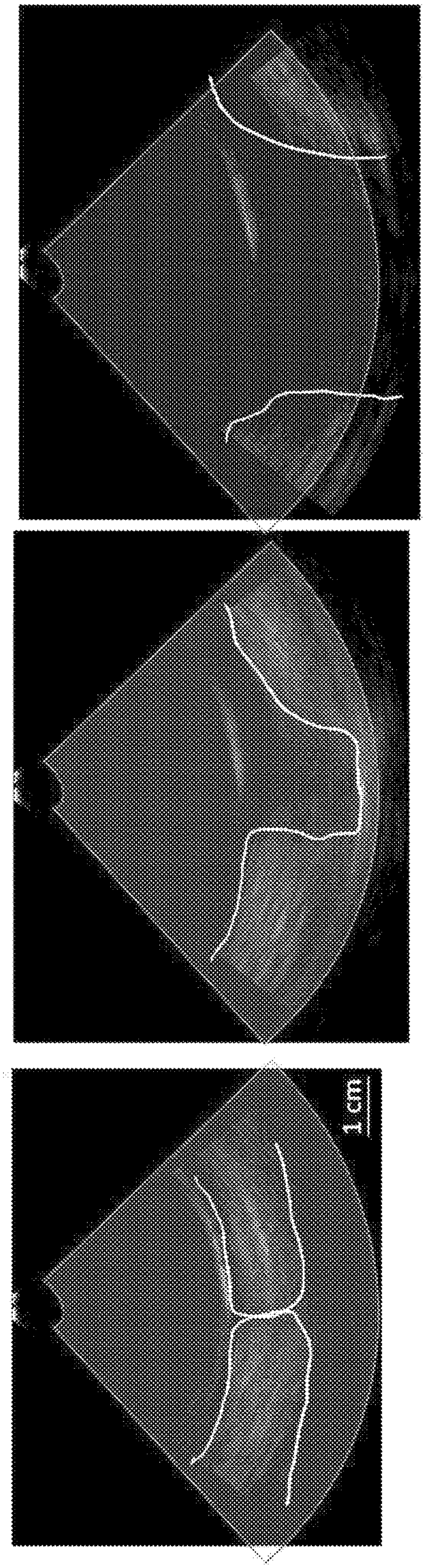
FIG. 2 shows ultrasound images of the cervix obtained using methods and systems as described herein (see FIG. 1) that correlate to cervical dilation during labor.
Figure 3:
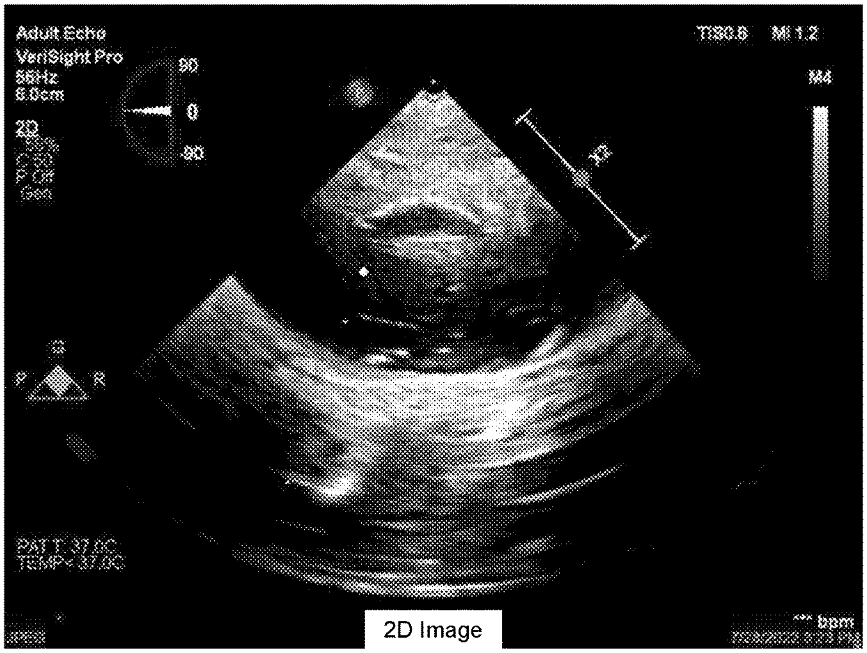
FIG. 3 shows ex vivo genito-urinary testing that was done using a 10 Fr US catheter showing 2D and 3D imaging with cervical dilation measurements.
Figure 3:
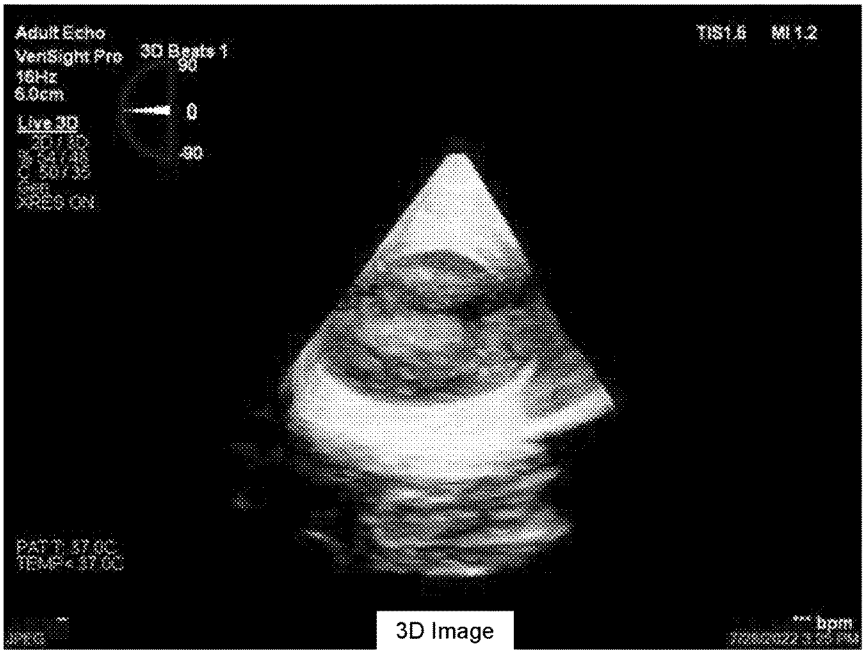
Figure 4:
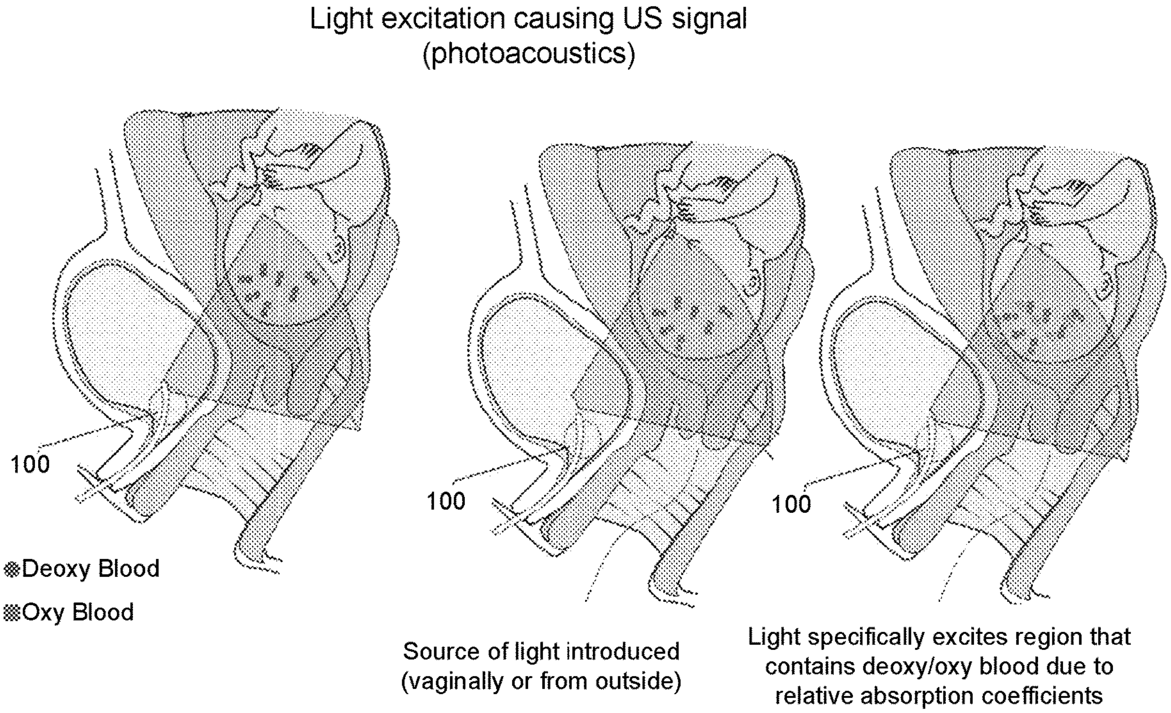
FIG. 4 shows an overview of a schematic of a device as described herein comprising an ultrasound transceiver inserted into the urethra and a light-emitting optical fiber inserted into the vagina that generates an optoacoustic signal.
Figure 5:
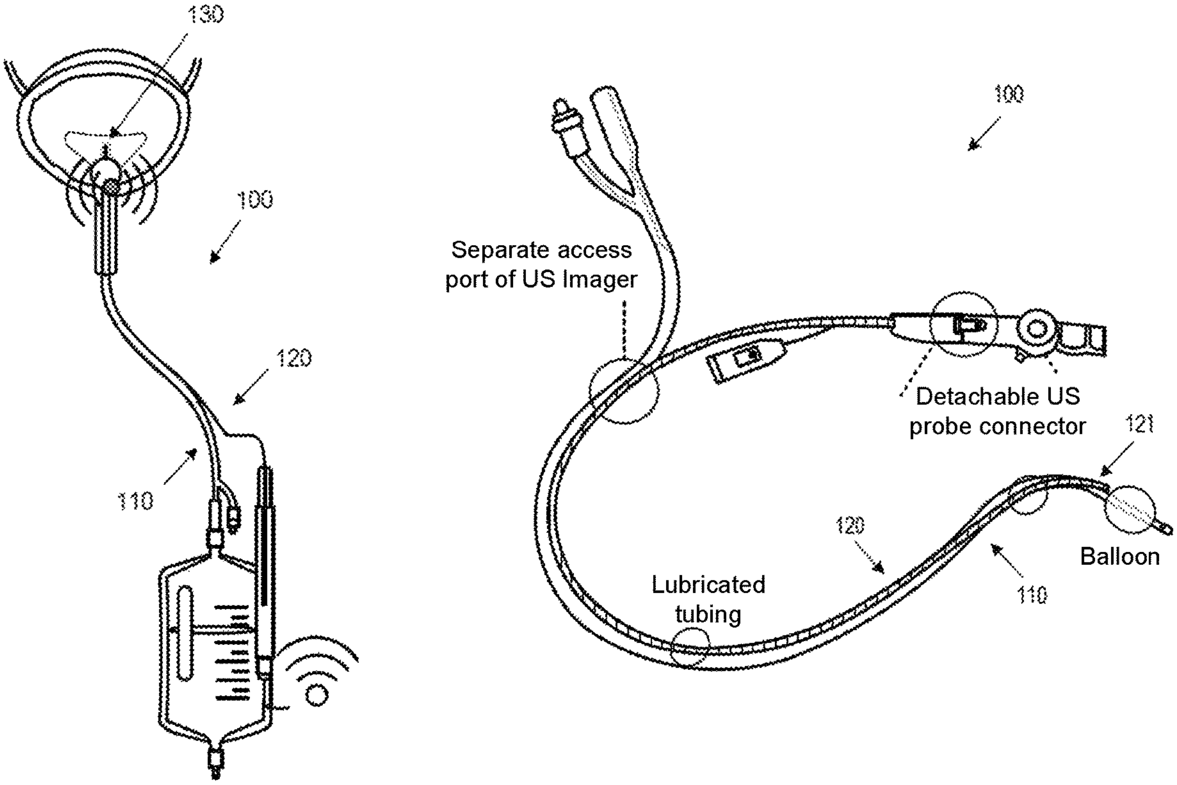
FIG. 5 shows a non-limiting embodiment that uses a detachable probe connected to a wireless ultrasound to display Wirelessly or via Bluetooth™ on an IPAD or screen.
Figure 6:
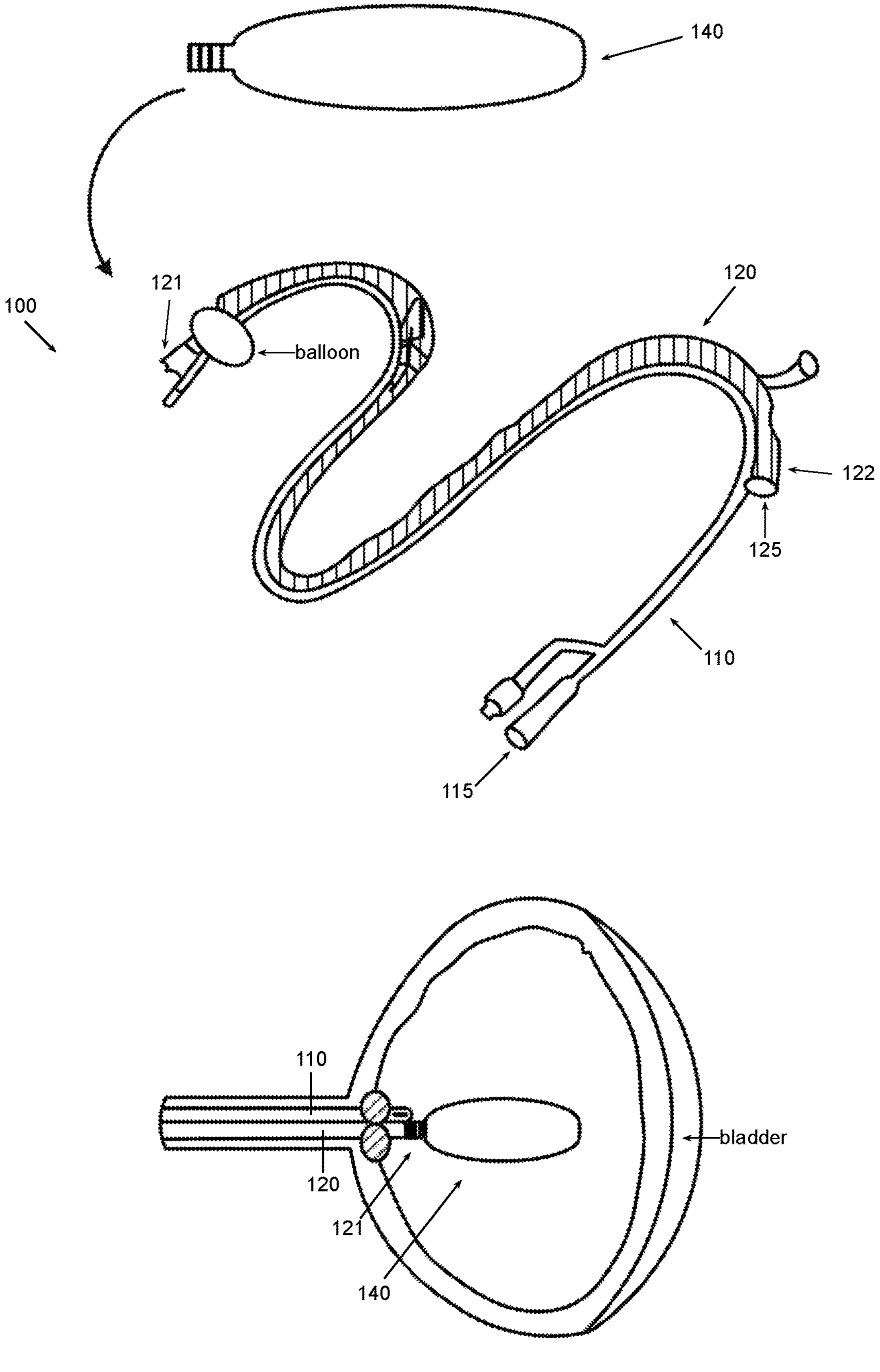
FIG. 6 shows a non-limiting embodiment of the system (100) for monitoring the progression of labor.
Figure 7:
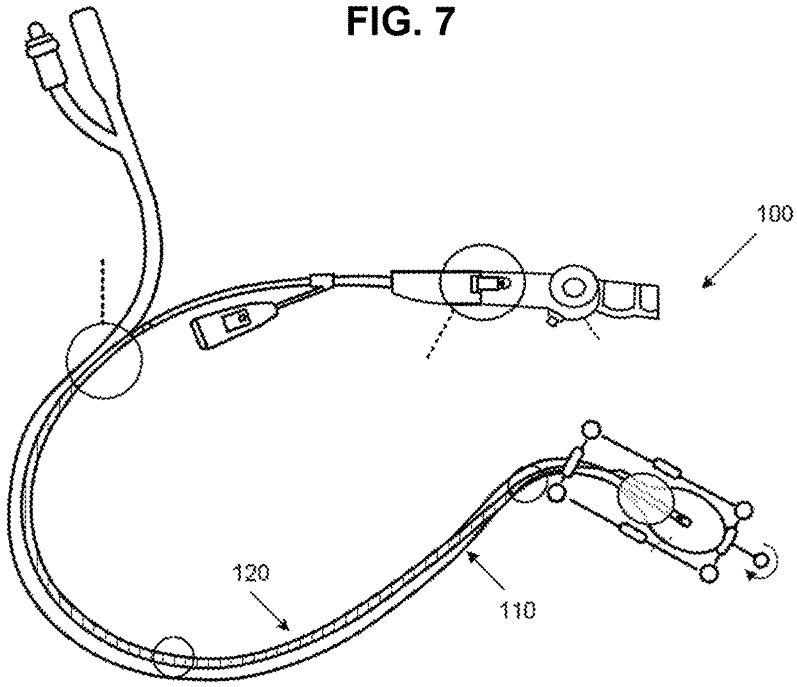
FIG. 7 shows a non-limiting embodiment that uses a separate lubricious port for a 5-9 Fr US probe while keeping the Foley catheter functioning independently.
Figure 8:
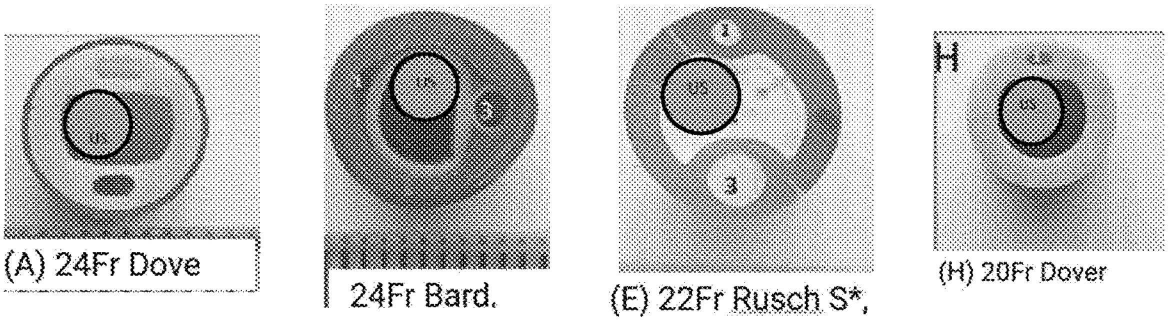
FIG. 8 shows potential designs for incorporating an ultrasound (US) into various catheter brands and sizes.
Figure 9:
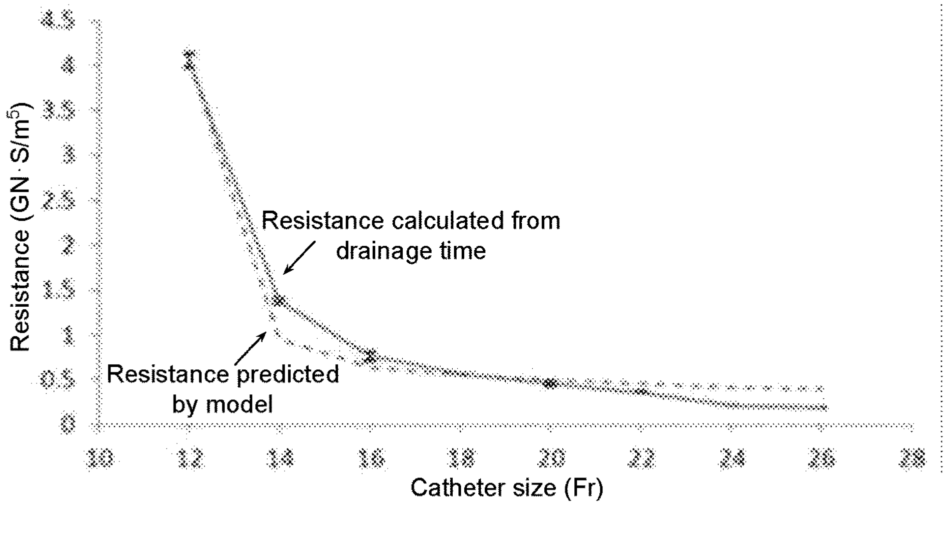
FIG. 9 shows a graph demonstrating catheter resistance versus catheter size.
Figure 10A:
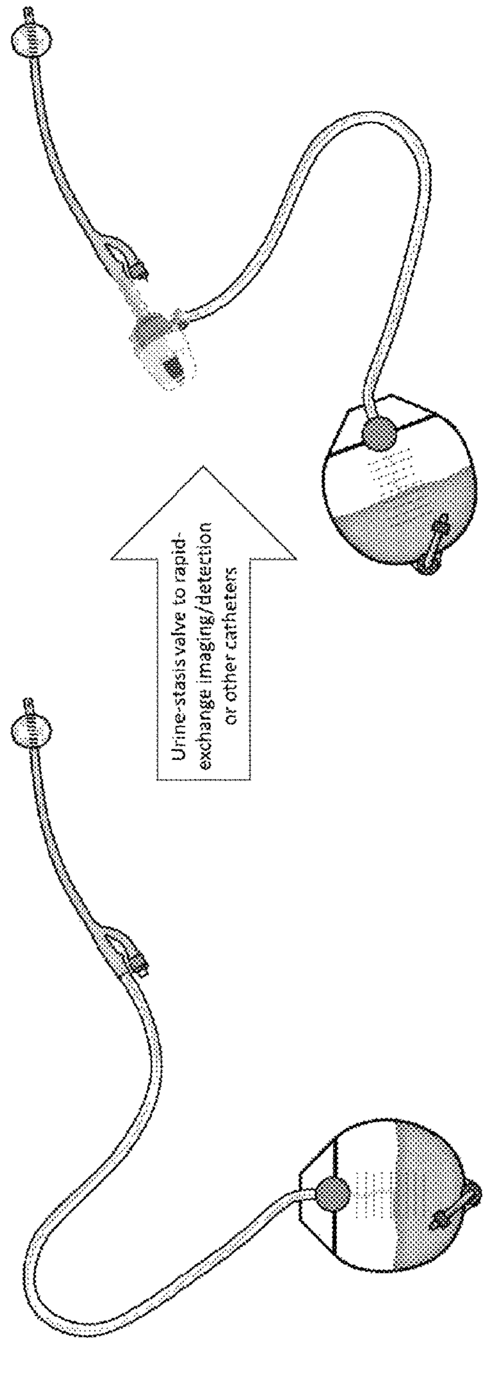
Figure 10B:
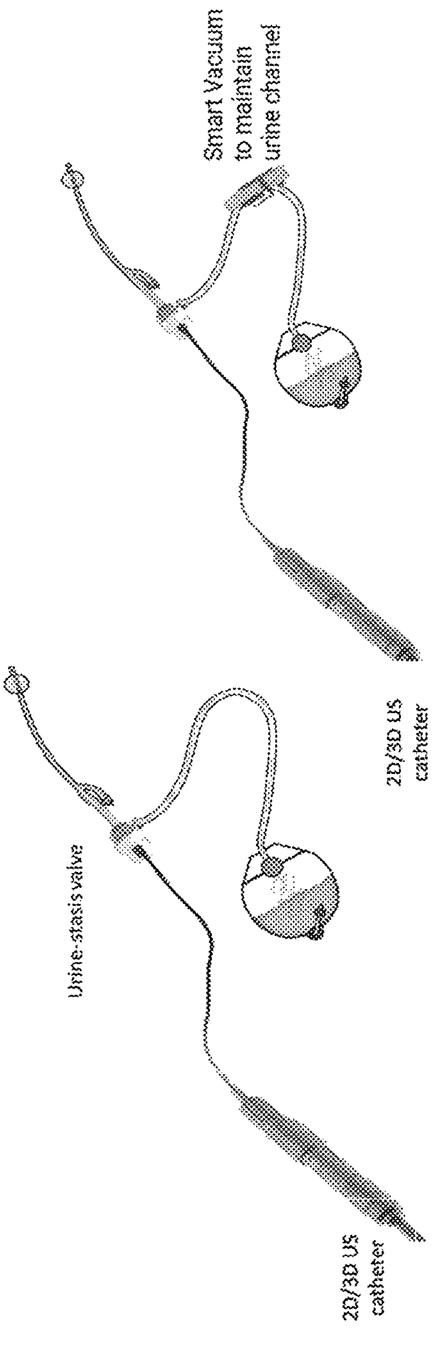
Figure 10C:
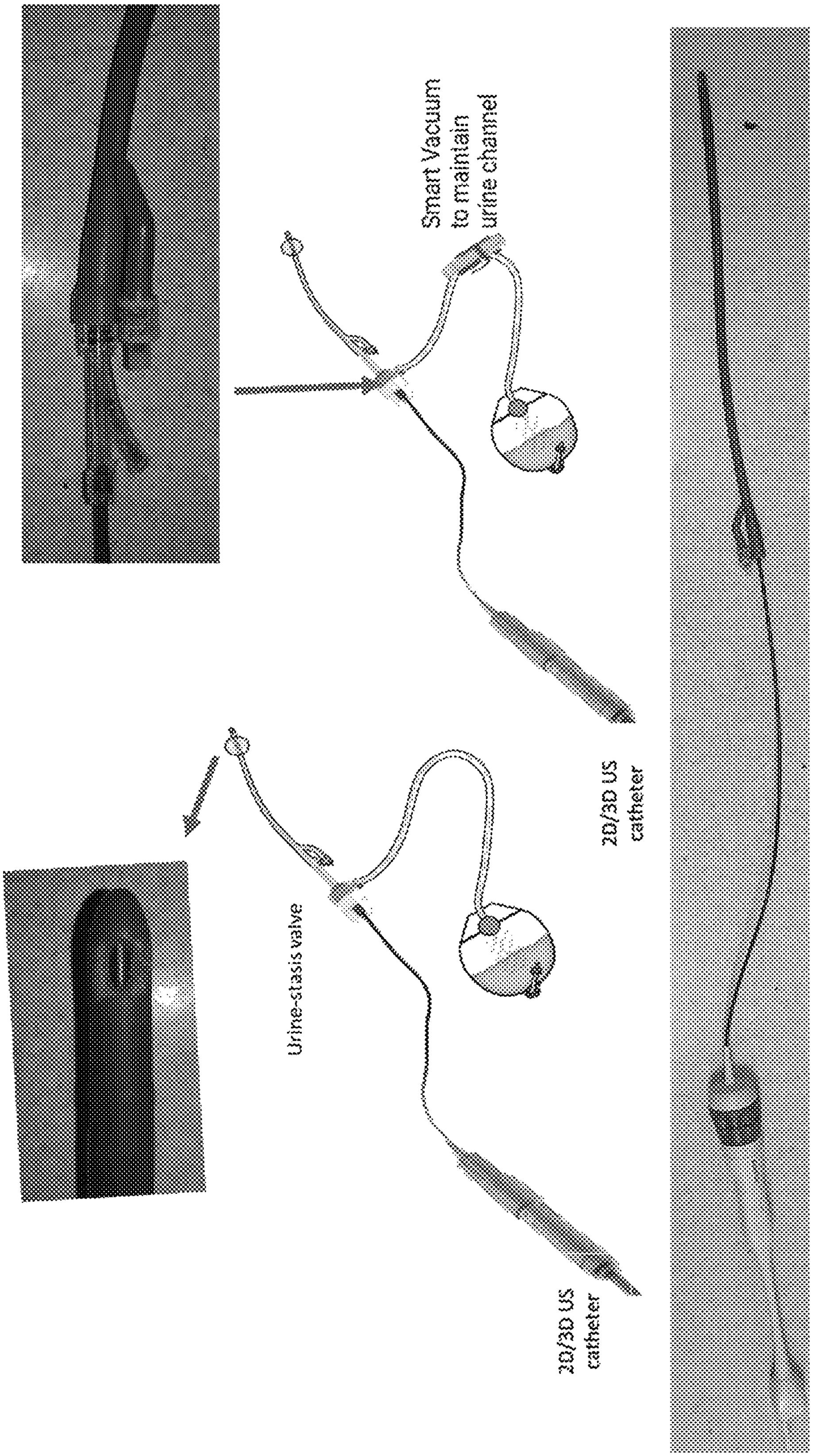

FIGS. 10A, 10B, and 10C show a simple "stasis" valve that allows for rapid-exchange of an imaging catheter (or any catheter). FIG. 10A shows an "urino-stasis" valve designed to connect between the urine bag and the urinary catheter. FIG. 10B shows an ultrasound imaging probe that fits through the lumen "urino-stasis" while the other port on the urino-stasis valve can drain the urine. FIG. 10C shows the port for draining urine may have a simple sensor mechanism to ensure flow to be constant with/without ultrasound imaging probe.

DETAILED DESCRIPTION OF THE INVENTION

Following is a list of elements corresponding to a particular element referred to herein:

100 System
110 Urinary Catheter
120 Working Channel
121 Distal End
122 Proximal End
125 Lumen
130 Ultrasound Transceiver Device
140 Cap Before the present compounds, compositions, and/or methods are disclosed and described, it is to be understood that this invention is not limited to specific synthetic methods or to specific compositions, as such may, of course, vary. It is also to be understood that the terminology used herein is for the purpose of describing particular embodiments only and is not intended to be limiting.

As used herein, the term "catheter" refers to a flexible, tubular medical device inserted through a narrow opening (e.g., the urethra) into a body cavity, particularly the bladder, to remove fluid. As used herein, "catheter," "urinary catheter," or "urethral catheter" may be used interchangeably.

As used herein, the terms "distal" and "proximal," as used in the following description with reference to a catheter or a working channel, relate to the position or orientation relative to a treating clinician. Thus, "proximal" refers to positions close to the clinician or pointing in a direction toward the clinician, and the term "distal" refers to positions that are far away or away from the clinician.

Referring now to FIGS. 1-8, the present invention features systems and methods that allow for an accurate and non-invasive way to determine cervical dilation as well as intrapartum fetal monitoring.

Monitoring System

The present invention features a system (100) for monitoring progression of labor and obtaining physiological measurements of the fetus during childbirth. The system may comprise a urinary catheter (110), a working channel (120) having a lumen (125) and removably attached to the catheter (110), and an ultrasound transceiver device (130) disposed in the lumen (125) of the working channel (120). The working channel has a lumen, a proximal end, and a distal end. In some embodiments, the ultrasound transceiver device (130) is configured to be inserted or removed from the working channel (120). In some embodiments, the system (100) further comprises a light-emitting optical fiber inserted into the lumen (125) of the working channel (120).

In some embodiments, the present invention features a system (100) for monitoring progression of labor and obtaining physiological measurements of the fetus during childbirth. The system may comprise a urinary catheter (110), a working channel (120) having a lumen (125) and removably attached to the catheter (110), and an ultrasound transceiver device (130) disposed in the lumen (125) of the working channel (120). The working channel (120) may have a lumen (125), a proximal end (122), a distal end (121), and a cap (140) attached to a distal end (121) of the working channel (120). In some embodiments, the ultrasound transceiver device (130) is configured to be inserted or removed from the working channel (120). In some embodiments, the system (100) further comprises a light-emitting optical fiber inserted into the lumen (125) of the working channel (120).

In some embodiments, the present invention features a system (100) for monitoring progression of labor and obtaining physiological measurements of the fetus during childbirth. The system may comprise a urinary catheter (110), a working channel (120) having a lumen (125) and permanently attached to the catheter (110), and an ultrasound transceiver device (130) disposed in the lumen (125) of the working channel (120). The working channel (120) may have a lumen (125), a proximal end (122), and a distal end (121). In some embodiments, the working channel (120) further comprises a cap (140) attached to a distal end (121) of the working channel (120). In some embodiments, the ultrasound transceiver device (130) is configured to be inserted or removed from the working channel (120). In some embodiments, the system (100) further comprises a light-emitting optical fiber inserted into the lumen (125) of the working channel (120).

In other embodiments, The system may comprise a urinary catheter (110), a working channel (120) having a lumen (125) and temporarily attached to the catheter (110), and an ultrasound transceiver device (130) disposed in the lumen (125) of the working channel (120). The working channel (120) may have a lumen (125), a proximal end (122), and a distal end (121). In some embodiments, the working channel (120) further comprises a cap (140) attached to a distal end (121) of the working channel (120). In some embodiments, the ultrasound transceiver device (130) is configured to be inserted or removed from the working channel (120). In some embodiments, the system (100) further comprises a light-emitting optical fiber inserted into the lumen (125) of the working channel (120).

In some embodiments, the working channel (120) is removably attached to the urinary catheter (110). In other embodiments, the working channel (120) is temporarily attached to the urinary catheter (110). In further embodiments, the working channel (120) is permanently attached to the urinary catheter (110). In some embodiments, the working channel (120) is detachable from the urinary catheter (110).

Without wishing to limit the present invention to any theory or mechanism, it is believed that embodiments in which the working channel (120) comprises a cap (140) allow for the ultrasound transceiver device (130) to be completely sterile. However, in embodiments in which the working channel (120) does not have a cap (140) or in which the cap (140) is detached from the working channel (120), the system may allow for the use of wires or stents for urologic procedures.

In some embodiments, the system comprises a urinary catheter (110), a working channel (120) having a lumen (125) attached to the catheter (110), and an ultrasound transceiver device (130) disposed in the lumen (125) of the working channel (120). Non-limiting methods of attaching the working channel (120) to the catheter (110) include but are not limited to clasp mechanisms, bands, or a combination thereof.

In some embodiments, the system (100) comprises a catheter (110) and an ultrasound transceiver device (130) inserted into a lumen of the catheter (110). In some embodiments, the system (100) further comprises a light-emitting optical fiber inserted into the lumen of the catheter (110).

In some embodiments, the catheter (110) ranges from 6 Fr to 20 Fr (French units) in size (i.e., outer diameter is 6 Fr to 20 Fr in size). In some embodiments, the catheter (110) ranges from 6 Fr to 20 Fr, 6 Fr to 18 Fr, 6 Fr to 16 Fr, 6 Fr to 14 Fr, 6 Fr to 12 Fr, 6 Fr to 10 Fr, 6 Fr to 8 Fr. In some embodiments, the catheter (110) is 6 Fr. In some embodiments, the catheter (110) is 8 Fr. In some embodiments, the catheter (110) is 10 Fr. In some embodiments, the catheter (110) is 12 Fr. In some embodiments, the catheter (110) is 14 Fr. In some embodiments, the catheter (110) is 16 Fr. In some embodiments, the catheter (110) is 18 Fr. In some embodiments, the catheter (110) is 20 Fr.

In some embodiments, the catheter (110) described herein may comprise at least one port, or at least two ports, or at least three ports, or at least four ports. In some embodiments, at least one port is for inflating a balloon at the distal tip of the catheter (110). In some embodiments, at least one port is for evacuating urine. In other embodiments, at least one port is for the placement of the ultrasound transceiver (130) and corresponding wires. Without wishing to limit the present invention to any theories or mechanisms, it is believed that the use of a catheter (110) with a specific port for the placement (i.e., insertion) of the ultrasound transceiver (130) allows for the same ultrasound transceiver (130) to be used with catheters (110) with varying port sizes. In some embodiments, the catheter (110) comprises an ultrasound transceiver (130) already incorporated into said catheter (110).

In some embodiments, the catheter (110) is a drainage catheter. In certain embodiments, the catheter (110) is a Foley catheter. In some embodiments, the Foley catheter ranges from 6 Fr to 20 Fr. In some embodiments, the Foley catheter comprises two or more ports. In some embodiments, one port is for inflating a balloon at the distal tip, and one port is for evacuating the urine. In other embodiments, the Foley catheter may comprise another port for the placement of an ultrasound transceiver (130) and corresponding wires.

In some embodiments, the catheter (110) may comprise an ultrasound transceiver device (130) and relevant ports for the catheter (110). In certain embodiments, the ultrasound transceiver (130) is placed in the lumen of the catheter (110). In other embodiments, the ultrasound transceiver is placed in a port within said catheter (110).

In some embodiments, the working channel (120) ranges from 5 Fr to 10 Fr (French units) in size (i.e., outer diameter is 5 Fr to 10 Fr in size). In some embodiments, the catheter (110) ranges from 5 Fr to 10 Fr, 5 Fr to 9 Fr, 5 Fr to 8 Fr, 5 Fr to 7 Fr, or 5 Fr to 6 Fr. In some embodiments, the catheter (110) is 5 Fr. In some embodiments, the catheter (110) is 6 Fr. In some embodiments, the catheter (110) is 7 Fr. In some embodiments, the catheter (110) is 8 Fr. In some embodiments, the catheter (110) is 9 Fr. In some embodiments, the catheter (110) is 10 Fr.

In some embodiments, the working channel (120) further comprises a cap (140) attached to a distal end (121) of the working channel (120). In some embodiments, the cap (140) is detachable from the distal end (121) of the working channel (120). In some embodiments, the cap (140) is made of silicone or a similar material. In some embodiments, the cap (140) is a balloon comprising a means for attachment to the distal end (121) of the working channel (120). In some embodiments, the balloon is clear, thus providing minimal resistance to ultrasound imaging. In some embodiments, the balloon is made of silicone or a similar material. In some embodiments, the balloon is made of a material that provides minimal resistance to ultrasound imaging.

Without wishing to limit the present invention to any theories or mechanisms, it is believed that the balloon attached to the distal end (121) of the working channel (120) prevents the ultrasound transceiver device (130) from going too far into the bladder causing perforation, avoids infection with the introduction of the ultrasound transceiver device (130), and allows the use of the ultrasound transceiver device (130) multiple times without reprocessing.

In some embodiments, the ultrasound transceiver device (130) is a Philips ultrasound device. In some embodiments, the ultrasound transceiver device (130) is a Viewflex™ (Abbott) ultrasound device. In some embodiments, the ultrasound transceiver device (130) is an Acuson ultrasound device. In some embodiments, the ultrasound transceiver device (130) is a Siemens ultrasound device. In some embodiments, the ultrasound transceiver device (130) is a Clarius ultrasound device. Other ultrasound devices may be used in accordance with the present invention. In some embodiments, the ultrasound transceiver device (130) comprises intracardiac echocardiography (ICE) capabilities.

In some embodiments, the ultrasound transceiver (130) is 3 French units (Fr) in size. In some embodiments, the ultrasound transceiver (130) is 4 French units (Fr) in size. In some embodiments, the ultrasound transceiver (130) is 5 French units (Fr) in size. In some embodiments, the ultrasound transceiver (130) is 6 French units (Fr) in size. In some embodiments, the ultrasound transceiver (130) is 7 French units (Fr) in size. In some embodiments, the ultrasound transceiver (130) is 8 French units (Fr) in size. In some embodiments, the ultrasound transceiver (130) is 9 French units (Fr) in size.

In some embodiments, the ultrasound transceiver (130) is able to fit within the working channel (120). In some embodiments, the ultrasound transceiver (130) is able to fit within the lumen (125) of the working channel (120). In other embodiments, the ultrasound transceiver (130) is able to fit within the catheter (110). In some embodiments, the ultrasound transceiver (130) is able to fit within the lumen of the catheter (110). In some embodiments, the ultrasound transceiver is able to fit within at least one port of the catheter (110). In other embodiments, the catheter (110) may be redesigned to allow for the placement of an ultrasound transceiver within said catheter.

In some embodiments, the ultrasound transceiver device (130) is inserted into the lumen (125) of the working channel (120) such that the end of the ultrasound transceiver device is at or near a distal end (121) of the working channel (120). In some embodiments, the distal end (121) of the working channel (120) is inserted into the urethra and into the bladder of the female. In some embodiments, the urinary catheter (110) comprises an open end that is inserted into the urethra and into the bladder of the female. In some embodiments, the ultrasound transceiver is connected to an ultrasound transceiver control module.

In some embodiments, the ultrasound transceiver (130) may be adjusted via pull wires, flexion mechanisms, or other mechanical manipulations to direct the ultrasound beams to obtain relevant measurements of the region of interest, like the cervix, baby, uterine regions, etc. In some embodiments, the directing of the ultrasound beams can be conducted electronically without the movement of the ultrasound transceiver (130).

In some embodiments, the ultrasound transceiver device (130) has the ability to lock into a particular position. In some embodiments, the cap (140) on the distal end (121) of the working channel (120) holds the ultrasound transceiver device (130) in a particular position (e.g., the cap (140) has the ability to hold the ultrasound transceiver device (130) in place). Without wishing to limit the present invention to any theory or mechanism, it is believed that the particular placement of the ultrasound transceiver device (130) allows for accurate measurements.

In some embodiments, the ultrasound transceiver device (130) transmits and receives ultrasound signals. In some embodiments, the ultrasound transceiver device (130) receives ultrasound signals. In other embodiments, the ultrasound transceiver device (130) receives optoacoustic signals. In further embodiments, the ultrasound transceiver (130) device receives both ultrasound signals and optoacoustic signals.

In some embodiments, the ultrasound transceiver transmits and receives sound signals. In other embodiments, the ultrasound transceiver receives photoacoustic signals generated by a light source. In some embodiments, the photoacoustic light signals may be used to determine physiological quantities including but not limited to blood oxygenation and heart rate of the intrapartum mother and/or the baby.

In preferred embodiments, the ultrasound transceiver device (130) transmits ultrasound signals at a range of about 7 MHz to 25 MHz. In some embodiments, the center frequency is about 7 MHz. In some embodiments, the ultrasound transceiver device (130) transmits ultrasound signals at about 5 MHz to 60 MHz. In some embodiments, the ultrasound transceiver device (130) transmits ultrasound signals at about 5 MHz to 50 MHz. In some embodiments, the ultrasound transceiver device (130) transmits ultrasound signals at about 5 MHz to 40 MHz. In some embodiments, the ultrasound transceiver device (130) transmits ultrasound signals at about 5 MHz to 30 MHz. In some embodiments, the ultrasound transceiver device (130) transmits ultrasound signals at about 5 MHz to 25 MHz. In some embodiments, the ultrasound transceiver device (130) transmits ultrasound signals at about 5 MHz to 10 MHz. In some embodiments, the ultrasound transceiver device (130) transmits ultrasound signals at about 10 MHz to 60 MHz. In some embodiments, the ultrasound transceiver device (130) transmits ultrasound signals at about 10 MHz to 50 MHz. In some embodiments, the ultrasound transceiver device (130) transmits ultrasound signals at about 10 MHz to 40 MHz. In some embodiments, the ultrasound transceiver device (130) transmits ultrasound signals at about 10 MHz to 30 MHz. In some embodiments, the ultrasound transceiver device (130) transmits ultrasound signals at about 10 MHz to 25 MHz. In some embodiments, the ultrasound transceiver device (130) transmits ultrasound signals at about 25 MHz to 60 MHz. In some embodiments, the ultrasound transceiver device (130) transmits ultrasound signals at about 25 MHz to 50 MHz. In some embodiments, the ultrasound transceiver device (130) transmits ultrasound signals at about 25 MHz to 40 MHz.

Without wishing to limit the present invention to any theories or mechanisms, it is believed that increasing the frequency of the signal transmitted from the ultrasound transceiver device (130) allows for a higher quality of images; however, the signal intensity is lower at deeper locations (e.g., location greater than 5 cm).

In some embodiments, the ultrasound transceiver (130) can transmit and receive signals from depths up to 5 cm or longer. In some embodiments, the ultrasound transceiver (130) can transmit and receive signals from depths up to 9 cm or longer. In some embodiments, the ultrasound transceiver (130) can transmit and receive signals from depths up to 15 cm or longer. In some embodiments, the ultrasound transceiver (130) can transmit and receive signals from depths ranging from about 5 cm to 20 cm, or about 5 cm to 15 cm, or about 5 cm to 10 cm, or about 10 cm to 20 cm, or about 10 cm to 15 cm, or about 15 cm to 20 cm. In some embodiments, lower ultrasound frequencies allow for signals to be transmitted and received at a farther depth; however, the resolution (i.e., the quality) of the images diminishes. In some embodiments, the ultrasound transceiver (130) has an image sector width of 90 degrees.

In some embodiments, the ultrasound transceiver (130) provides an image with a resolution of 0.1 mm. In some embodiments, the ultrasound transceiver (130) provides an image with a resolution of 0.05 mm. In other embodiments, the ultrasound transceiver (130) provides an image with a resolution of 0.03 mm. In some embodiments, the ultrasound transceiver (130) provides an image with a resolution of about 0.1 mm to 0.03 mm.

As the resolution of the images provided by the ultrasound transceiver (130) decreases, the depth at which different structures can be seen increases. Conversely, as the resolution of the images provided by the ultrasound transceiver (130) increases, the depth at which different structures can be seen decreases. In some embodiments, an appropriate resolution may be chosen based on the depth of the structures needed to be seen using the ultrasound transceiver device (130) described herein.

Without wishing to limit the present invention to any theories or mechanisms, it is believed that the quality or resolution of the ultrasound image improves as the elevation of the ultrasound ultrasound transceiver (130) face increases (e.g., 9 Fr will have a higher ultrasound elevation compared to a 7 Fr and therefore a 9 Fr ultrasound transceiver (130) will have an image quality (e.g., higher resolution and higher quality) that is better compared to a 7 Fr ultrasound transceiver (130)), forgoing any other changes in the parameters (i.e., all other parameters remain the same).

As used herein, "ultrasound elevation" refers to azimuthal resolution and represents the extent to which an ultrasound system is able to resolve objects within an axis perpendicular to the plane formed by the axial and lateral dimensions. The elevational axis represents the height or "thickness" of the beam.

The monitoring systems (100) described herein may further comprise a light source. In some embodiments, the light source is a light-emitting optical fiber. In some embodiments, the monitoring system (100) may comprise at least one light source (e.g., light-emitting optical fiber).

In some embodiments, the light source is inserted into the working channel (120). In some embodiments, the light source is inserted into the lumen (125) of the working channel (120). In other embodiments, the light source is placed outside the urinary bladder. For example, the light source may be placed near or inside the vaginal canal, near the belly to allow for external illumination, near the pubic region pointing toward the uterus, or other regions of interest.

In other embodiments, the light source is inserted into the catheter (110; e.g., the lumen of the catheter (110). In some embodiments, the light source is inserted into a port of the catheter (110). In other embodiments, the light source is placed outside the catheter (110).

In some embodiments, the resultant ultrasound signal generated from the light source (e.g., the light-emitting optical fiber) is recorded at the tip of the ultrasound transceiver (130).

In some embodiments, the ultrasound transceiver device (130) is configured to receive photoacoustic signals generated by a light source. In some embodiments, the light source is a light-emitting optical fiber. In other embodiments, the light-emitting optical fiber propagates a photoacoustic light source. In some embodiments, the photoacoustic light source is a photoacoustic excitation light. In some embodiments, the photoacoustic light source propagates in the optical fiber. In some embodiments, the optical fiber carrying photoacoustic light is inserted into the catheter.

In some embodiments, the light source/receiver fiber(s) (<0.3 Fr) can be incorporated into the working channel (120) and perform diffused optical spectral measurements to obtain light and/or spectral information after the light interacts with cervical tissue, baby (intrapartum) and mother's cervical tissue regions. In some embodiments, the light source/receiver fiber(s) (<0.3 Fr) can be incorporated into the catheter (110) and perform diffused optical spectral measurements to obtain light and/or spectral information after the light interacts with cervical tissue, baby (intrapartum) and mother's cervical tissue regions. In other embodiments, the ultrasound transceiver device (130) image can aid in conducting relevant optical simulations incorporating the light source/receive fiber(s) to obtain information like tissue oxygenation or blood oxygenation from speckles of light received, the intensity of light received, the intensity of light received across the fibers.

In certain embodiments, the system (100) comprises a catheter (110) and an ultrasound transceiver device (130) inserted into a lumen of the catheter (110). In some embodiments, the system (100) further comprises a urine-stasis valve designed to facilitate rapid fluid exchange from the proximal end to the distal end via the lumen of the urinary catheter (110). This allows for imaging with the ultrasound transceiver device (130) through the lumen of the urinary catheter (110).

In certain embodiments, the system (100) comprises a catheter (110) and an ultrasound transceiver device (130) inserted into a lumen of the catheter (110). In some embodiments, the ultrasound transceiver device (130; e.g., the ultrasound probe) incorporates a working channel (120) having a distal end (121), and a proximal end (122). In some embodiments, the ultrasound transceiver device (130; e.g., the ultrasound probe) features a urine-stasis valve designed to facilitate rapid fluid exchange from the proximal end (122) to the distal end (121) via the working channel (120). This allows for imaging with the ultrasound probe (130) through the working channel.

In some embodiments, the system (100) may comprise an additional smart vacuum on the proximal end to enhance the suction in order to account for the ultrasound transceiver device (130) being inserted into the lumen of the urinary catheter (110).

Methods

The present invention features a method of monitoring progression of labor and obtaining physiological measurements of a fetus during childbirth. The method comprises inserting a monitoring system (100) into a urethra of a pregnant female during labor and obtaining physiological measurements of a cervical region and a uterus region of the pregnant female during labor. In some embodiments, the monitoring system (100) comprises a urinary catheter (110), a working channel (120) removably attached to the catheter (110), and an ultrasound transceiver device (130) disposed in the lumen (125) of the working channel (120). In other embodiments, the monitoring system (100) comprises a urinary catheter (110), a working channel (120) attached to the catheter (110; e.g., permanently attached to the catheter (110) or temporarily attached to the catheter (110)), and an ultrasound transceiver device (130) disposed in the lumen (125) of the working channel (120). In further embodiments, the monitoring system (100) comprises a urinary catheter (110) and an ultrasound transceiver device (130) disposed in the lumen of the urinary catheter (110). In some embodiments, the working channel (120) has a lumen (125), a proximal end (122), and a distal end (121). In other embodiments, the working channel (120) has a lumen (125), a proximal end (122), a distal end (121), and a cap (140) attached to a distal end (121) of the working channel (120).

In some embodiments, the method further comprises inserting a light-emitting optical fiber into the lumen (125) of the working channel (120). In some embodiments, the method further comprises inserting a light-emitting optical fiber into the lumen of the catheter (110).

In some embodiments, the present invention features a method of monitoring progression of labor and obtaining physiological measurements of the fetus and/or the mother during childbirth. In some embodiments, the method comprises inserting a catheter (110) into a urethra of a pregnant female during labor, inserting an ultrasound transceiver device (120) into the lumen of the catheter (110), and obtaining physiological measurements of a cervical region and a uterus region of the pregnant female during labor. In some embodiments, the method further comprises inserting a light-emitting optical fiber into the catheter.

In some embodiments, the ultrasound transceiver device (130) transmits and receives ultrasound signals. In other embodiments, the ultrasound transceiver device (130) receives optoacoustic signals. In further embodiments, the ultrasound transceiver (130) device receives both ultrasound signals and optoacoustic signals.

In some embodiments, the methods described herein comprise inserting an ultrasound transceiver device (130)

into a working channel (120; e.g., into the lumen (125) of the working channel (120)). In some embodiments, the methods described herein comprise inserting a light source (e.g., into the light-emitting optical fiber) into a working channel (120; e.g., into the lumen (125) of the working channel (120)). In further embodiments, the methods described herein comprise inserting an ultrasound transceiver device (130) and a light source into a working channel (120; e.g., into the lumen (125) of the working channel (120)). In some embodiments, the methods described herein comprise inserting an ultrasound transceiver device (130) and/or a light source into a working channel (120; e.g., into the lumen (125) of the working channel (120)). In some embodiments, the ultrasound transceiver device (130) is configured to receive photoacoustic signals generated by the light source (e.g., the light-emitting optical fiber).

In some embodiments, the methods described herein comprise inserting an ultrasound transceiver device (130) into a catheter (110; e.g., into the lumen of the catheter (110)). In some embodiments, the methods described herein comprise inserting a light source (e.g., the light-emitting optical fiber) into a catheter (110; e.g., into the lumen of the catheter (110)). In further embodiments, the methods described herein comprise inserting an ultrasound transceiver device (130) and a light source into a catheter (110; e.g., into the lumen of the catheter (110)). In some embodiments, the methods described herein comprise inserting an ultrasound transceiver device (130) and/or a light source into a catheter (110; e.g., into the lumen of the catheter (110)). In some embodiments, the ultrasound transceiver device is configured to receive photoacoustic signals generated by the light source (e.g., the light-emitting optical fiber).

In some embodiments, the ultrasound transceiver (130) may be inserted into the working channel (120; e.g., into the lumen (125) of the working channel (120)) before the insertion and placement of the monitoring system (100; e.g., the catheter (110) removably attached to the working channel (120)). In other embodiments, the ultrasound transceiver (130) may be inserted into the working channel (120; e.g., into the lumen (125) of the working channel (120)) after the insertion and placement of the monitoring system (100) in the urinary bladder.

The monitoring system (100) may be placed initially in a desired urinary bladder location. For example, the monitoring system (100) may be inserted into the urinary bladder such that an ultrasound transceiver (130) is placed in an optimized location to perform physiological measurements in the cervical region (like effacement, dilation measurements, etc.), uterus regions, and for intrapartum fetal monitoring.

In some embodiments, the ultrasound transceiver (130) may be placed in different locations and orientations depending on which structures (e.g., the uterus, baby, or cervical regions) need to be monitored. For example, ultrasound transceiver (130) signals may be directed for the measurement of cervical dilation and cervical effacement. Closer placement of the ultrasound transceiver (130) to the cervical region while still being inside the urinary bladder will increase photoacoustic and ultrasound signal amplitude. In some embodiments, the ultrasound transceiver (130) may be adjusted via pull wires, flexion mechanisms, or other mechanical manipulations to direct the ultrasound beams to obtain relevant measurements of the region of interest like, the cervix, baby, uterine regions, etc. In some embodiments, the directing of the ultrasound beams can be conducted electronically without the movement of the ultrasound transceiver (130).

In certain embodiments, the ultrasound transceiver (130) may be inserted into the catheter (110; e.g., into the lumen of the catheter (110)) before the insertion and placement of the catheter (110). In other embodiments, the ultrasound transceiver (130) may be inserted into the catheter (110; e.g., into the lumen of the catheter (110)) after the insertion and placement of the catheter (110).

In some embodiments, the catheter (110) may be inserted into the urinary bladder such that an ultrasound transceiver (130) is placed in an optimized location to perform physiological measurements in the cervical region (like effacement, dilation measurements, etc.), uterus regions, and for intrapartum fetal monitoring. In some embodiments, the ultrasound transceiver (130) is within the catheter (110). In some embodiments, the catheter (110) is able to perform its regular function of emptying the urinary bladder, while the ultrasound transceiver (130) is within the catheter (110).

In some embodiments, the methods described herein may be used in assessing the Bishop score. As used herein, the "Bishop score" is a pre-labor scoring system to assist in predicting whether induction of labor will be required. The Bishop score is a traditional method for determining the readiness of a cervix to dilate before labor induction. In some embodiments, the Bishop score may be used in addition to the position of the fetus, softening and shortening of the cervix, and the location of the presenting part of the baby to determine the readiness of a cervix to dilate. Likewise, it can be used to assess if the laboring female is meeting milestones for induction or for failed induction.

In some embodiments, the methods described herein allow for a more accurate determination of the Bishop score. In other embodiments, the methods described herein allow for a more accurate and frequent update of the parameter used to measure the Bishop score.

In some embodiments, the methods described herein may be used for assessing the physiological cervical ripening that predates spontaneous uterine contractions associated with effacement. In other embodiments, the methods described herein may be used for assessing the opening of the internal cervical os (dilatation) and softening of the cervix (consistency).

In some embodiments, the methods described herein comprise obtaining physiological measurements of a cervical region and a uterus region of the pregnant female during labor. In some embodiments, physiological measurements may include but are not limited to maternal contraction strength and variability, cervical dilation, effacement, thickness, shape, placental position compared to internal cervical os, fetal lie and fetal presentation, fetal head position, engagement and progression of the fetal head, internal rotation, fetal head extension, fetal heart rate, fetal heart rate monitoring, fetal oxygen saturation, or a combination thereof.

Methods herein may further comprise obtaining the blood oxygen level of the pregnant female and/or the baby. In certain embodiments, the ultrasound transceiver device (130) receives photoacoustic signals generated by a light source. The photoacoustic light signals may be used to determine physiological quantities including but not limited to blood oxygenation and heart rate of the intrapartum mother and/or the baby. In some embodiments, methods herein utilize a light source for generating chromophores (e.g., blood, oxygenated blood, deoxygenation blood, lipid, etc.). In some embodiments, the ultrasound transceiver (130) placed at or near the distal end (e.g., the distal end (121) of the working channel (120) is able to measure relevant quantities of blood oxygenation, blood volume, blood flow, lipid concentration, etc., of both the intrapartum mother and the baby/babies.

In some embodiments, the light source allows for photoacoustic excitation and may be placed so that structures of the uterus, cervical region, and baby (intrapartum) are illuminated with said photoacoustic excitation light source to specifically excite chromophores and measure the sonic response through the ultrasound transceiver near the distal portion of the catheter. In some embodiment, a "sonic response" refers to an ultrasound wave generated at the chromophore and its amplitude measured at the ultrasound transceiver (130) location (e.g., after the ultrasound wave travels from the chromophore to the ultrasound transceiver (130)). In some embodiments, a sonic response refers to the ultrasonic wave generated as a result of a short (e.g., nanosecond duration) pulsed light absorbed by the chromophore (e.g., blood comprising oxyhemoglobin and deoxyhemoglobin). Different amplitudes of the signal will be generated depending on the light wavelength. For example, oxygenated blood (i.e., blood comprising oxyhemoglobin) absorbs light at a wavelength of 532 nm at ten ns pulse duration will generate a sonic pressure wave at the blood vessel, which travels omnidirectionally until it reaches the ultrasound transceiver location and its amplitude is measured. Additionally, for example, 950 nm is absorbed by oxyhemoglobin, 770 nm is absorbed by deoxyhemoglobin.

In some embodiments, the photoacoustic excitation light is absorbed by tissue chromophores. In some embodiments, the tissue chromophores include oxy-hemoglobin, deoxy-hemoglobin, or a combination thereof. In other embodiments, the tissue chromophores generate a sonic wave that is measured by the ultrasound transceiver device (130).

In some embodiments, the methods and systems described herein allow for accurately measuring cervical dilation. In other embodiments, the methods and systems described herein allow for intrapartum fetal monitoring. In further embodiments, the methods and systems described herein allow for monitoring the blood oxygenation of the fetus and/or the pregnant female.

As used herein, the term "about" refers to plus or minus 10% of the referenced number.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of," and as such the written description requirement for claiming one or more embodiments of the present invention using the phrase "consisting essentially of" or "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A system (100) for monitoring progression of labor, the system comprising:

a. a urinary catheter (110);

a. a working channel (120) attached and extending along at least a portion of the urinary catheter (110), the working channel (120) having a lumen (125), a proximal end (122), a distal end (121), and a cap (140) attached to the distal end (121) of the working channel (120);

a. an ultrasound transceiver device (130) disposed within the lumen (125) of the working channel (120) and configured to image a cervical region, a uterus region, or both; and a. a urino-stasis valve fluidically connected to the urinary catheter (110). the urino-stasis valve comprising a first port configured to receive the ultrasound transceiver device (130) and a second port configured to drain urine;

wherein the cap (140) comprises a clear balloon configured to provide minimal resistance to ultrasound imaging and configured to prevent the ultrasound transceiver device (130) from causing perforation of a bladder wall, wherein the cap (140) is further configured to maintain sterility of the ultrasound transceiver device (130) within the lumen (125) of the working channel (120); and wherein the progression of labor is monitored using the images captured by the ultrasound transceiver device (130).

2. The system (100) of claim 1, wherein the working channel (120) is temporarily attached or permanently attached to the urinary catheter (110).

3. The system (100) of claim 1, wherein the working channel (120) is detachable from the urinary catheter (110).

4. The system (100) of claim 1, wherein the cap (140) is detachable.

5. The system (100) of claim 1, further comprising an ultrasound transceiver control module operably connected to the ultrasound transceiver device (130).

6. The system (100) of claim 1, wherein an end of the ultrasound transceiver device is at or near a distal end (121) of the working channel (120).

7. The system (100) of claim 1, wherein the ultrasound transceiver device (130) is configured to be inserted or removed from the working channel (120).

8. A method of monitoring progression of labor, the method comprising:

a. inserting a monitoring system (100) into a urethra of a pregnant female during labor; wherein the monitoring system (100) comprises:

i. a urinary catheter (110);

ii. a working channel (120) attached and extending along the at least a portion of the catheter, the working channel (120) having a lumen (125), a proximal end (122), a distal end (121), and a cap (140) attached to the distal end (121) of the working channel (120);

iii. an ultrasound transceiver device (130) disposed within the lumen (125) of the working channel (120) and configured to image a cervical region, a uterus region, or both, and wherein the cap (140) comprises a clear balloon configured to provide minimal resistance to ultrasound imaging and configured to prevent the ultrasound transceiver device (130) from causing perforation of a bladder wall, wherein the cap (140) is further configured to maintain sterility of the ultrasound transceiver device (130) within the lumen (125) of the working channel (120); and iv. a urino-stasis valve fluidically connected to the urinary catheter (110), the urino-stasis valve comprising a first port configured to receive the ultrasound transceiver device (130) and a second port configured to drain urine; and b. monitoring the progression of labor using the images captured by the ultrasound transceiver device (130) while shielding the bladder wall from perforation using the cap (140).

9. The method of claim 8, further comprises connecting the ultrasound transceiver device (130) to an ultrasound transceiver control module.

10. The method of claim 8, wherein the ultrasound transceiver device transmits ultrasound signals at 7 MHz to 25 MHz.

11. The method of claim 8, wherein the ultrasound transceiver device transmits ultrasound signals at a depth of 9 cm.

12. The method of claim 8, further comprises creating a 3D ultrasound image using the ultrasound transceiver device (130).

13. The method of claim 8 further comprises introducing a light source, wherein the light source is inserted into the lumen (125) of the working channel (120).

14. The method of claim 13, wherein the ultrasound transceiver device (130) is configured to receive photoacoustic signals generated by the light source.

15. The method of claim 14, wherein the light source is a light-emitting optical fiber configured to propagate a photoacoustic light source, wherein the photoacoustic light source is a photoacoustic excitation light.

16. The method of claim 8, wherein monitoring the progression of labor comprises measuring cervical dilation, cervical effacement, cervical thickness, cervical shape, placental position compared to internal cervical os, fetal lie and fetal presentation, fetal head position, engagement and progression of the fetal head, internal rotation, fetal head extension, fetal heart rate, or a combination thereof.

17. A system (100) for monitoring progression of labor, the system consisting of:

a. a urinary catheter (110);

b. a working channel (120) attached and extending along at least a portion of the urinary catheter (110), the working channel (120) having a lumen (125), a proximal end (122), a distal end (121), and a cap (140) attached to the distal end (121) of the working channel (120);

c. an ultrasound transceiver device (130) disposed within the lumen (125) of the working channel (120) and configured to image a cervical region, a uterus region, or both; and d. a urino-stasis valve fluidically connected to the urinary catheter (110), the urino-stasis valve comprising a first port configured to receive the ultrasound transceiver device (130) and a second port configured to drain urine;

wherein the cap (140) comprises a clear balloon configured to provide minimal resistance to ultrasound imaging and configured to prevent the ultrasound transceiver device (130) from causing perforation of a bladder wall, wherein the cap (140) is further configured to maintain sterility of the ultrasound transceiver device (130) within the lumen (125) of the working channel (120); and wherein the progression of labor is monitored using the images captured by the ultrasound transceiver device (130).

* * * * *